(12) United States Patent
Uchida et al.

(10) Patent No.: US 7,767,827 B2
(45) Date of Patent: Aug. 3, 2010

(54) PYRAZOLE-1-CARBOXYLATE DERIVATIVES, PROCESS FOR THE PRODUCTION THEREOF AND PROCESS FOR THE PRODUCTION OF PYRAZOLE DERIVATIVES

(75) Inventors: Atsushi Uchida, Tokyo (JP); Wakako Yokota, Kanagawa (JP); Kenji Hirai, Kanagawa (JP); Tomoyuki Yano, Shizuoka (JP)

(73) Assignees: Kaken Pharmaceutical Co., Ltd. (JP); Sagami Chemical Research Center (JP)

( * ) Notice: Subject to any disclaimer, the term of this patent is extended or adjusted under 35 U.S.C. 154(b) by 216 days.

(21) Appl. No.: 11/915,016

(22) PCT Filed: May 22, 2006

(86) PCT No.: PCT/JP2006/310600

§ 371 (c)(1),
(2), (4) Date: Dec. 21, 2007

(87) PCT Pub. No.: WO2006/126692

PCT Pub. Date: Nov. 30, 2006

(65) Prior Publication Data

US 2009/0018345 A1    Jan. 15, 2009

(30) Foreign Application Priority Data

May 23, 2005    (JP) ............................. 2005-148889

(51) Int. Cl.
*C07D 231/10*    (2006.01)
(52) U.S. Cl. ................................. 548/369.7; 548/374.1
(58) Field of Classification Search .............. 548/369.7, 548/374.1
See application file for complete search history.

(56) References Cited

U.S. PATENT DOCUMENTS

| 4,298,749 | A  | 11/1981 | Plath et al. |
| 4,316,040 | A  | 2/1982  | Plath et al. |
| 4,320,132 | A  | 3/1982  | Cecere et al. |
| 6,294,567 | B1 | 9/2001  | Hashizume et al. |
| 2005/0014813 | A1 | 1/2005 | Tawada et al. |
| 2005/0070441 | A1 | 3/2005 | Hirai et al. |

FOREIGN PATENT DOCUMENTS

| WO | 00/07997 A1 | 2/2000 |
| WO | 02/46182 A1 | 6/2002 |
| WO | 02/066446 A1 | 8/2002 |
| WO | 03/099793 A1 | 12/2003 |

*Primary Examiner*—Kamal A Saeed
*Assistant Examiner*—Samantha L Shterengarts
(74) *Attorney, Agent, or Firm*—Nixon Peabody LLP

(57) ABSTRACT

Disclosed are pyrazole-1-carboxylate derivatives of the general formula (1),

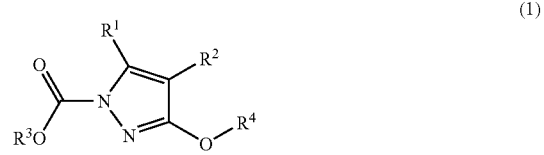

(1)

(wherein symbols are as defined in the specification),
a process for the production thereof and processes for producing herbicidally active 3-aryloxypyrazole-1-carboxamide derivatives from the above compound and an intermediate therefor.

According to this invention, there can be industrially advantageously produced 3-aryloxypyrazole-1-carboxamide derivatives that does not cause chemical damage on crops but exhibits excellent herbicidal activity against weeds that impair the growth of such crops.

7 Claims, No Drawings

PYRAZOLE-1-CARBOXYLATE DERIVATIVES, PROCESS FOR THE PRODUCTION THEREOF AND PROCESS FOR THE PRODUCTION OF PYRAZOLE DERIVATIVES

CROSS-REFERENCE TO RELATED APPLICATIONS

This application is a 371 National Phase Entry Application of co-pending International Application PCT/JP2006/310600, filed 22 May 2006, which designated the U.S. and which claims the benefit under 35 U.S.C. §119 of Japanese Patent Application No. 2005-148889, filed 23 May 2005.

TECHNICAL FIELD

The present invention relates to pyrazole-1-carboxylate derivatives, a process for the production thereof and a process for the production of pyrazole derivatives, in particular pyrazole derivatives having herbicidal activities and intermediates thereof.

The pyrazole-1-carboxylate derivatives of the present invention are the compounds that are useful as intermediates for the production of 3-aryloxypyrazole-1-carboxamide derivatives useful as herbicide active ingredients.

BACKGROUND ART

3-Aryloxypyrazole-1-carboxamides useful as herbicide active ingredients are produced by O-arylation of the hydroxy group at the 3-position of 3-hydroxypyrazole and subsequent N-carbamoylation on the nitrogen atom at the 1-position of the pyrazole ring (International Patent Publication No. 02/066439). In the above production route, however, the regioselectivity for the O-arylation is poor and a byproduct is formed in which arylation has taken place on the nitrogen atom at the 1-position of the pyrazole ring, so that it cannot necessarily be said that the above process is industrially desirable.

Of compounds of the following general formula (I),

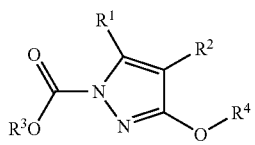

(1)

there is described ethyl 3-hydroxypyrazole-1-carboxylates which is the compounds of the general formula (I) in which $R^2$ and $R^4$ are hydrogen atoms and $R^1$ is a methyl group, in which $R^2$ and $R^4$ are hydrogen atoms and $R^1$ is a propyl group or in which $R^2$ is an ethyl group, $R^4$ is a hydrogen atom and $R^1$ is a methyl group. However, no process for the production thereof is described in detail (see U.S. Pat. No. 4,320,132).

DISCLOSURE OF THE INVENTION

Under the circumstances, it is an object of the present invention to provide pyrazole-1-carboxylate derivatives useful as the intermediates for the production of 3-aryloxypyrazole-1-carboxamide derivatives useful as herbicide active ingredients, and it is a second object of the present invention to provide a process for the industrial production thereof.

Further, it is a third object of the present invention to provide a process for the production of pyrazole derivatives such as pyrazole derivatives having herbicidal activities and intermediates thereof.

For achieving the above objects, the present inventors have made diligent studies and as a result have found that the desired aryl group can be introduced on the hydroxy group at the 3-position of 3-hydroxypyrazole derivatives with high selectivity and yield by introducing an alkoxycarbonyl group on the nitrogen atom at the 1-position of 3-hydroxypyrazole derivatives followed by O-arylation. It has been further found that the thus-obtained 3-aryloxypyrazole-1-carboxylates can be easily converted to herbicidally active 3-aryloxypyrazole-1-carboxamide derivatives by removing ester moiety at the 1-position followed by carbamoylation.

That is, the present invention provides (1) pyrazole-1-carboxylate derivatives of the general formula (I),

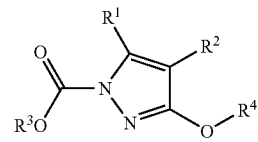

(1)

wherein $R^1$ is a hydrogen atom or an optionally substituted alkyl group having 1 to 6 carbon atoms, $R^2$ is a hydrogen atom, a halogen atom or an optionally substituted alkyl group having 1 to 6 carbon atoms, $R^3$ is an optionally substituted alkyl group having 1 to 6 carbon atoms and $R^4$ is a hydrogen atom, an optionally substituted phenyl group or an optionally substituted pyridyl group, provided that the case of $R^3$ being an ethyl group is excluded when $R^2$ and $R^4$ are hydrogen atoms and $R^1$ is a methyl group, when $R^2$ and $R^4$ are hydrogen atoms and $R^1$ is a propyl group or when $R^2$ is an ethyl group, $R^4$ is a hydrogen atom and $R^1$ is a methyl group, (2) a process for the production of 3-hydroxypyrazole-1-carboxylate derivatives of the general formula (4),

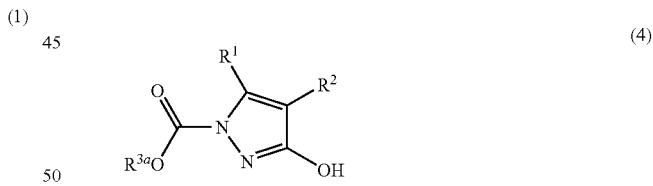

(4)

wherein $R^1$ and $R^2$ are as defined above and $R^{3a}$ is an optionally substituted alkyl group having 1 to 6 carbon atoms, which comprises reacting 3-hydroxypyrazole derivatives of the general formula (2),

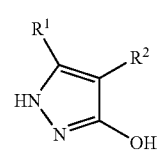

(2)

wherein R¹ and R² are as defined above, with dialkyl dicarbonates of the general formula (3),

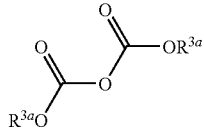
(3)

wherein $R^{3a}$ is as defined above, (to be sometimes referred to as "production process 1" hereinafter), (3) a process for the production of 3-aryloxypyrazole-1-carboxylate derivatives of the general formula (1a),

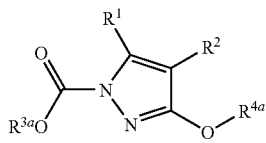
(1a)

wherein R¹, R² and $R^{3a}$ are as defined above and $R^{4a}$ is an optionally substituted phenyl group or an optionally substituted pyridyl group, which comprises reacting 3-hydroxypyrazole-1-carboxylate derivatives of the general formula (4),

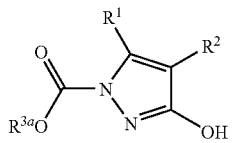
(4)

wherein R¹, R² and $R^{3a}$ are as defined above, with aryl halides of the general formula (5), $R^{4a}$-Z  (5)

wherein $R^{4a}$ is as defined above and Z is a halogen atom, in the presence of a base, (to be sometimes referred to as "production process 2" hereinafter), (4) a process for the production of 3-aryloxypyrazole derivatives of the general formula (6),

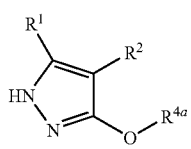
(6)

wherein R¹, R² and $R^{4a}$ are as defined above, which comprises hydrolyzing 3-aryloxypyrazole-1-carboxylate derivatives of the general formula (1a),

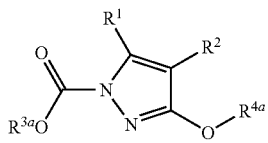
(1a)

wherein R¹, R², $R^{3a}$ and $R^{4a}$ are as defined above, (to be sometimes referred to as "production process 3" hereinafter), and (5) a process for the production of pyrazole derivatives of the general formula (8),

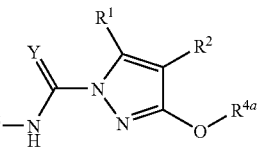
(8)

wherein R¹, R² and $R^{4a}$ are as defined above, $R^5$ is an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms, an optionally substituted phenyl group, an optionally substituted alkyloxy group having 1 to 6 carbon atoms, an optionally substituted cycloalkyloxy group having 3 to 8 carbon atoms, an optionally substituted aralkyloxy group having 7 to 11 carbon atoms, an optionally substituted alkenyloxy group having 3 to 6 carbon atoms, an optionally substituted alkynyloxy group having 3 to 6 carbon atoms or an optionally substituted phenyloxy group and Y is an oxygen atom or a sulfur atom, which comprises hydrolyzing 3-aryloxypyrazole-1-carboxylate derivatives of the general formula (1a),

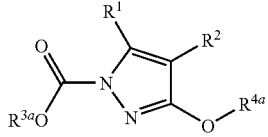
(1a)

wherein R¹, R², $R^{3a}$ and $R^{4a}$ are as defined above, to obtain 3-aryloxypyrazole derivatives of the general formula (6),

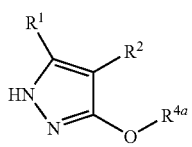
(6)

wherein $R^1$, $R^2$ and $R^{4a}$ are as defined above, and then reacting this product with isocyanates or isothiocyanates of the general formula (7), $$R^5-NCY \qquad (7)$$

wherein $R^5$ and Y are as defined above, (to be sometimes referred to as "production process 4" hereinafter).

PREFERRED EMBODIMENTS OF THE INVENTION

Pyrazole-1-carboxylate derivatives of the present invention are the compounds having a structure of the general formula (1),

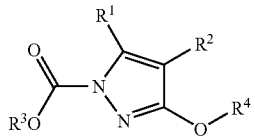

wherein $R^1$ is a hydrogen atom or an optionally substituted alkyl group having 1 to 6 carbon atoms, $R^2$ is a hydrogen atom, a halogen atom or an optionally substituted alkyl group having 1 to 6 carbon atoms, $R^3$ is an optionally substituted alkyl group having 1 to 6 carbon atoms and $R^4$ is a hydrogen atom, an optionally substituted phenyl group or an optionally substituted pyridyl group, provided that the case of $R^3$ being an ethyl group is excluded when $R^2$ and $R^4$ are hydrogen atoms and $R^1$ is a methyl group, when $R^2$ and $R^4$ are hydrogen atoms and $R^1$ is a propyl group or when $R^2$ is an ethyl group, $R^4$ is a hydrogen atom and $R^1$ is a methyl group.

In the above general formula (1), the optionally substituted alkyl group having 1 to 6 carbon atoms, represented by each of $R^1$, $R^2$ and $R^3$, may be linear or branched, and examples thereof include methyl, ethyl, propyl, isopropyl, butyl, isobutyl, sec-butyl, tert-butyl, pentyl, isoamyl, neopentyl, 1-ethylpropyl, 1-methylbutyl, 2-methylbutyl, hexyl, isohexyl, 2-ethylbutyl and 4-methylpentyl groups.

Examples of the halogen atom represented by $R^2$ include halogen atoms such as a fluorine atom, a chlorine atom and a bromine atom.

Examples of the substituted phenyl group, represented by $R^4$, include phenyl groups which may have, as a substituent on the benzene ring, a halogen atom, an alkyl group having 1 to 12 carbon atoms, a haloalkyl group having 1 to 6 carbon atoms, an acyl group having 1 to 6 carbon atoms, an alkyl group having 1 to 12 carbon atoms and being substituted with an alkyloxyimino group having 1 to 4 carbon atoms, an alkyloxycarbonyl group having 1 to 6 carbon atoms, a carboxy group, a cyano group, a substituted amino group, an alkyloxy group having 1 to 6 carbon atoms, an aryloxy group, a haloalkyloxy group having 1 to 6 carbon atoms, an alkylthio group having 1 to 6 carbon atoms, an alkylsulfinyl group having 1 to 6 carbon atoms, an alkylsulfonyl group having 1 to 6 carbon atoms, a haloalkylthio group having 1 to 6 carbon atoms, a haloalkylsulfinyl group having 1 to 6 carbon atoms, a haloalkylsulfonyl group having 1 to 6 carbon atoms and a nitro group. Of these substituents on the benzene ring, electron-withdrawing substituents such as a trifluoromethyl group, a nitro group, a cyano group, a chlorine atom, a fluorine atom, an alkoxycarbonyl group, etc., are preferred in that they serve to achieve good production yields, and the position(s) on which these electron-withdrawing substituent(s) is to be substituted is preferably the o-position and/or the p-position.

More specifically, examples of the above optionally substituted phenyl group include 4-fluorophenyl, 4-chlorophenyl, 4-bromophenyl, 2,4-difluorophenyl, 2,4-dichlorophenyl, 2,4,5-trichlorophenyl, 2-chloro-5-trifluoromethylphenyl, 2-trifluoromethylphenyl, 4-trifluoromethylphenyl, 2,4-bis(trifluoromethyl)phenyl, 2,6-dichloro-4-trifluoromethylphenyl, 4-cyanophenyl, 4-cyano-2-trifluoromethylphenyl, 2-methylthiophenyl, 4-methylthiophenyl, 2-methylsulfinylphenyl, 4-methylsulfinylphenyl, 2-methylsulfonylphenyl, 4-methylsulfonylphenyl, 4-trifluoromethylthiophenyl, 4-trifluoromethylsulfinylphenyl, 4-trifluoromethylsulfonylphenyl, 2-nitrophenyl, 4-nitrophenyl, 2-nitro-4-trifluoromethylphenyl, 4-nitro-2-trifluoromethylphenyl, 4-nitro-3-trifluoromethylphenyl, 2,6-dichloro-4-trifluorometehylphenyl, 2-chloro-6-fluoro-4-trifluoromethylphenyl, 2-chloro-6-nitro-4-trifluoromethylphenyl and 2,4-dinitro-6-trifluoromethylphenyl groups. Concerning these substituents on the benzene ring, for example, a nitro group can be converted to an amino group by reduction, and further, the amino group can be converted to a halogen atom or a substituted alkyl group via a diazonium salt.

Examples of the optionally substituted pyridyl group, represented by $R^4$, include pyridyl groups which may have, as a substituent on the pyridine ring, a halogen atom, an alkyl group having 1 to 12 carbon atoms, a haloalkyl group having 1 to 6 carbon atoms, a cyano group, an alkyloxy group having 1 to 6 carbon atoms and a nitro group. Of these substituents on the pyridine ring, electron-withdrawing substituents such as a trifluoromethyl group, a nitro group, a cyano group, a chlorine atom, a fluorine atom, an alkoxycarbonyl group, etc., are preferred in that they serve to achieve good production yields and that they are commercially available as raw materials, and the position(s) on which these electron-withdrawing substituent(s) is to be substituted is preferably the 3-position and/or the 5-position of the pyridine ring.

More specifically, examples of the above optionally substituted pyridyl group include 3-chloropyridin-2-yl, 5-chloropyridin-2-yl, 3,5-dichloropyridin-2-yl, 4-amino-3,5-dichloropyridin-2-yl, 3-cyano-6-methylpyridin-2-yl, 5-trifluoromethylpyridin-2-yl, 3-chloro-5-trifluoromethylpyridin-2-yl, 3-nitropyridin-2-yl, 5-nitropyridin-2-yl, 3-nitro-4-methylpyridin-2-yl, 3-nitro-6-methoxypyridin-2-yl, 2-chloro-3-nitropyridin-6-yl, 6-chloro-3-nitropyridin-2-yl and 3,5-dinitropyridin-2-yl groups.

When the pyrazole-1-carboxylate derivatives of the above general formula (1) is used as intermediates for the pyrazole derivatives having herbicidal activities, preferably, $R^1$ is a methyl group, $R^2$ is a hydrogen atom and $R^3$ is an alkyl group having 1 to 4 carbon atoms, or preferably $R^4$ is a hydrogen atom, 2-chloro-6-fluoro-4-trifluoromethylphenyl group or 2,6-dichloro-4-trifluoromethylphenyl group.

The production process 1 of the present invention will be explained below. The production process 1 is a process in which 3-hydroxypyrazole derivatives of the general formula (2),

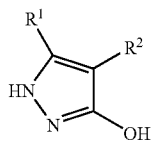

(2)

wherein $R^1$ and $R^2$ are as defined above, and dialkyl carbonates of the general formula (3),

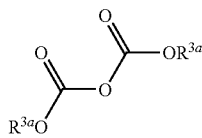

(3)

wherein $R^{3a}$ is an optionally substituted alkyl group having 1 to 6 carbon atoms, are allowed to react, thereby to produce 3-hydroxypyrazole-1-carboxylate derivatives of the general formula (4),

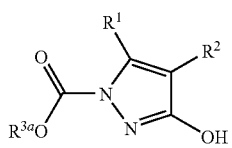

(4)

wherein $R^1$, $R^2$ and $R^{3a}$ are as defined above.

The above optionally substituted alkyl group having 1 to 6 carbon atoms represented by $R^{3a}$ is as already explained with regard to the above $R^3$.

A reaction scheme in the above production process 1 is shown below.

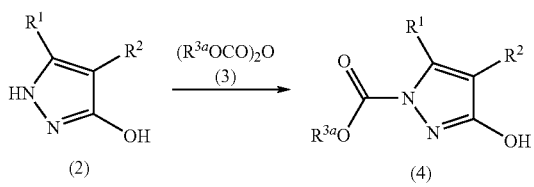

wherein $R^1$, $R^2$ and $R^{3a}$ are as defined above.

This reaction can be carried out in a solvent. The solvent can be selected from any solvents that do not cause any detrimental effect on the reaction, and it can be selected from aromatic hydrocarbon solvents such as benzene, toluene, xylene, chlorobenzene, etc., aliphatic hydrocarbon solvents such as pentane, hexane, octane, etc., ether solvents such as diethyl ether, diisopropyl ether, cyclopentyl methyl ether, tetrahydrofuran (THF), dimethoxyethane (DME), 1,4-dioxane, etc., ketones such as acetone, methyl ethyl ketone, cyclohexanone, etc., halogen-containing solvents such as chloroform, dichloromethane, nitrile solvents such as acetonitrile, propionitrile, etc., ester solvents such as ethyl acetate, propyl acetate, butyl acetate, methyl propionate, etc., amide solvents such as N,N-dimethylformamide (DMF), N,N-dimethylacetamide, N-methylpyrrolidone, etc., alcohol solvents such as methanol, ethanol, isopropyl alcohol, etc., DMSO or mixtures of these.

The yield of this reaction can be improved when it is carried out in the presence of a base. The base can be selected from organic bases such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane, imidazole, etc., and alkali metal bases such as sodium carbonate, potassium carbonate, sodium bicarbonate, potassium bicarbonate, sodium acetate, potassium acetate, sodium methoxide, sodium ethoxide, potassium-tert-butoxide, sodium hydride, potassium hydride, sodium amide, butyl lithium, tert-butyl lithium, lithium diisopropylamide, trimethylsilyl lithium, lithium hexamethyldisilazide, etc. When the reaction is carried out using 0.1 to 3 mol equivalents of the base to the substrate, the desired product can be obtained in good yields.

The reaction temperature is not specially limited, while the desired product can be obtained in good yields when the reaction is carried out at a temperature selected from the range of 0° C. to 150° C. While the thus-obtained product can be used in the subsequent reaction without further purification, it may be purified by recrystallization or the like if necessary.

Pyrazole derivatives of the general formula (2) for use as a raw material in the above reaction can be easily produced, for example, by the cyclization reaction of hydrazine and a β-ketoester derivative according a method described in Organic Synthesis, Collective Volume, 6, 791 (1988). The 3-hydroxypyrazole-1-carboxylate derivative exists as an equilibrium mixture of tautomers, while its general formula is depicted as a structure of an alcohol form for convenience.

When 3-hydroxypyrazole-1-carboxylate derivatives of the above general formula (4) is used as an intermediate for a herbicidally active pyrazole derivative, preferably, $R^1$ is methyl, $R^2$ is a hydrogen atom and $R^{3a}$ is an alkyl group having 1 to 4 carbon atoms.

The production process 2 of the present invention will be explained below. This production process 2 is a process in which 3-hydroxypyrazole-1-carbonate derivatives of the general formula (4),

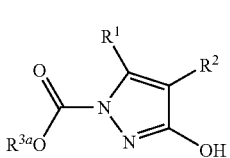

(4)

wherein $R^1$, $R^2$ and $R^{3a}$ are as defined above, and aryl halides of the general formula (5), $R^{4a}$-Z (5)

wherein $R^{4a}$ is an optionally substituted phenyl group or an optionally substituted pyridyl group and Z is a halogen atom, are reacted in the presence of a base, to produce 3-aryloxy-pyrazole-1-carboxylate derivatives of the general formula (1a),

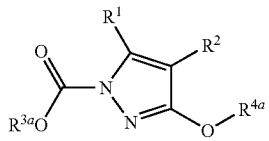

(1a)

wherein $R^1$, $R^2$, $R^{3a}$ and $R^{4a}$ are as defined above.

The optionally substituted phenyl group or optionally substituted pyridyl group represented by the above $R^{4a}$ is as explained with regard to the above $R^4$. Examples of the halogen atom represented by Z include a fluorine atom, a chlorine atom, a bromine atom, etc.

A reaction scheme in the above production process 2 is shown below.

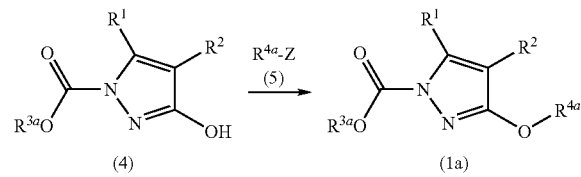

wherein $R^1$, $R^2$, $R^{3a}$, $R^{4a}$ and Z are as defined above.

This reaction is carried out in the presence of a base as an agent for trapping hydrogen halide. The base can be selected from alkali metal bases such as sodium hydride, sodium amide, sodium carbonate, potassium carbonate, sodium methoxide, sodium ethoxide, potassium-tert-butoxide, sodium hydroxide, potassium hydroxide, etc., or organic amines such as triethylamine, tributylamine, N-methylmorpholine, pyridine, dimethylaniline, etc. While the amount of the base to be used is not specially limited, the reaction is carried out using more than one equivalent of the base to the reaction substrate, whereby the desired product can be obtained in good yields.

The reaction can be carried out in a solvent, and any solvent can be used so long as it has no detrimental effect on the reaction. The solvent can be selected, for example, from ether solvents such as diethyl ether, THF, 1,4-dioxane, DME, etc., nitrile solvents such as acetonitrile, propionitrile, etc., esters such as ethyl acetate, ethyl propionate, etc., aromatic hydrocarbon solvents such as benzene, toluene, xylene, chlorobenzene, etc., amides such as DMF, N-methylpyrrolidone, etc., DMSO, water or mixtures of these solvents. Of these, DMF and DMSO are preferred in that good yields are attained.

The reaction temperature is not specially limited, while the reaction is carried out at a temperature selected from the range of 0° C. to 150° C., and in this case the desired product can be obtained in good yields. After completion of the reaction, the desired product can be obtained by general post-treatment procedures. It can be purified by column chromatography, recrystallization, etc., if necessary.

When 3-aryloxypyrazole-1-carboxylate derivatives of the above general formula (1a) is used as an intermediate for a herbicidally active pyrazole derivative, preferably, $R^1$ is a methyl group, $R^2$ is a hydrogen atom and $R^{3a}$ is an alkyl group having 1 to 4 carbon atoms, and preferably, $R^{4a}$ is 2-chloro-6-fluoro-4-trifluoromethylphenyl or 2,6-dichloro-4-trifluoromethylphenyl group.

The production process 3 of the present invention will be explained below. This production process 3 is a process in which 3-aryloxypyrazole-1-carboxylate derivatives of the general formula (1a),

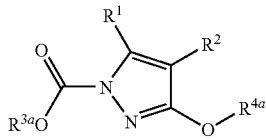

(1a)

wherein $R^1$, $R^2$, $R^{3a}$ and $R^{4a}$ are as defined above, are hydrolyzed to produce 3-aryloxypyrazole derivatives of the general formula (6),

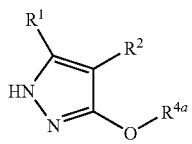

(6)

wherein $R^1$, $R^2$, and $R^{4a}$ are as defined above.

A reaction scheme in the above production process 3 is shown below.

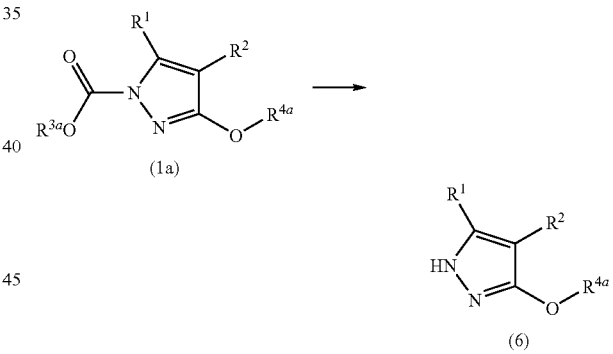

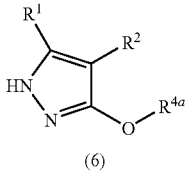

wherein $R^1$, $R^2$, $R^{3a}$ and $R^{4a}$ are as defined above.

This hydrolyzing reaction can be carried out under an acidic or basic condition. The acid to be used is not specially limited, and it can be selected, for example, from inorganic acids such as hydrochloric acid, sulfuric acid, phosphoric acid, etc. There is no special limitation to be imposed on the amount of the acid to be used. There is no special limitation to be imposed on the base to be used, either, and it can be selected, for example, from inorganic bases such as sodium hydroxide, potassium hydroxide, calcium hydroxide, etc. There is no special limitation to be imposed on the amount of the base to be used. When $R^{3a}$ is a tert-alkyl group, the hydrolysis is carried out under an acidic condition, and in any other cases, the hydrolysis is preferably carried out under a basic condition.

The above reaction can be carried out in a solvent. Any solvent can be used so long as it has no detrimental effect on the reaction. It can be selected from aromatic hydrocarbon solvents such as benzene, toluene, xylene, chlorobenzene, etc., aliphatic hydrocarbon solvents such as pentane, hexane, octane, etc., ether solvents such as diethyl ether, diisopropyl ether, cyclopentyl methyl ether, THF, DME, 1,4-dioxane, etc., ketones such as acetone, methyl ethyl ketone, cyclohexanone, etc., halogen-containing solvents such as chloroform, dichloromethane, etc., nitrile solvents such as acetonitrile, propionitrile, etc., ester solvents such as ethyl acetate, propyl acetate, butyl acetate, methyl propionate, etc., amide solvents such as DMF, N,N-dimethylacetamide, N-methylpyrrolidone, etc., alcohol solvents such as methanol, ethanol, isopropyl alcohol, etc., DMSO or mixtures of these solvents.

While the reaction temperature is not specially limited, the reaction is carried out at a temperature selected from the range of 50° C. to 150° C., whereby the desired product can be obtained in good yields. The product can be used in the subsequent reaction without further purification, while it may be purified by recrystallization, etc., if necessary.

When 3-aryloxypyrazole derivatives of the above general formula (6) is used as an intermediate for a herbicidally active pyrazole derivative, preferably, $R^1$ is a methyl group and $R^2$ is a hydrogen atom, or preferably $R^{4a}$ is 2-chloro-6-fluoro-4-trifluoromethylphenyl or 2,6-dichloro-4-trifluoromethylphenyl group.

The production process 4 of the present invention will be explained below. This production process 4 is a process in which 3-aryloxypyrazole-1-carboxylate derivatives of the general formula (1a),

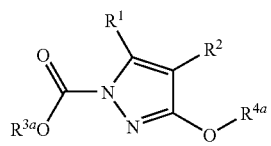

(1a)

wherein $R^1$, $R^2$, $R^{3a}$ and $R^{4a}$ are as defined above, are hydrolyzed to produce 3-aryloxypyrazole derivatives of the general formula (6),

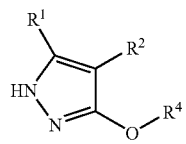

(6)

wherein $R^1$, $R^2$ and $R^{4a}$ are as defined above, and then the compounds are reacted with isocyanates or isothiocyanates of the general formula (7), $$R^5-NCY$$ (7)

wherein $R^5$ is an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms, an optionally substituted phenyl group, an optionally substituted alkyloxy group having 1 to 6 carbon atoms, an optionally substituted cycloalkyloxy group having 3 to 8 carbon atoms, an optionally substituted aralkyloxy group having 7 to 11 carbon atoms, an optionally substituted alkenyloxy group having 3 to 6 carbon atoms, an optionally substituted alkynyloxy group having 3 to 6 carbon atoms or an optionally substituted phenyloxy group and Y is an oxygen atom or a sulfur atom, to produce pyrazole derivatives of the general formula (8),

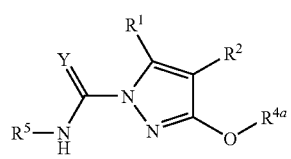

(8)

wherein $R^1$, $R^2$, $R^{4a}$, $R^5$ and Y are as defined above.

The alkyl group having 1 to 12 carbon atoms, represented by the above $R^5$, may be linear or branched, and examples thereof include methyl, ethyl, propyl, isopropyl, butyl, isobutyl, s-butyl, t-butyl, pentyl, isoamyl, neopentyl, 1-ethylpropyl, 1-methylbutyl, 2-methylbutyl, hexyl, isohexyl, 2-ethylbutyl, 4-methylpentyl, heptyl, 1-methylhexyl, octyl, decyl, undecyl and dodecyl groups, etc. The above alkyl group may have at least one substituent such as a halogen atom, a cycloalkyl group having 3 to 8 carbon atoms, a cyano group, a nitro group, an alkylthio group having 1 to 6 carbon atoms, an alkyloxy group having 1 to 6 carbon atoms, a tetrahydrofurfuryl group, an alkyloxycarbonyl group having 1 to 6 carbon atoms, a carboxy group, an acyl group, etc., and more specifically, examples of the optionally substituted alkyl group include 2-chloroethyl, 2-bromoethyl, 3-chloropropyl, 3-fluoropropyl, cyclopropylmethyl, cyclopentylmethyl, cyclohexylmethyl, cyanomethyl, 2-cyanoethyl, 3-cyanopropyl, nitromethyl, 2-methylthioethyl, methoxymethyl, ethoxymethyl, 2-methoxyethyl, 2-chloroethoxymethyl, tetrahydrofurfuryl, methoxycarbonylmethyl, ethoxycarbonylmethyl, 1-methoxycarbonylethyl, 1-ethoxycarbonylethyl, 2-ethoxycarbonylethyl, carboxymethyl, acetonyl, 1-acetylethyl, 3-acetylpropyl, phenacyl, 4-chlorophenacyl, 2,4-difluorophenacyl, 4-methylphenacyl, 4-isopropylphenacyl, 4-isobutylphenacyl, 4-cyclohexylphenacyl, 4-cyanophenacyl and 4-nitrophenacyl groups, etc.

Examples of the cycloalkyl group having 3 to 8 carbon atoms, represented by $R^5$, include cyclopropyl, cyclobutyl, cyclopentyl, cyclohexyl and cyclooctyl groups, etc., and these cycloalkyl group may be substituted with a halogen atom, an alkyl group having 1 to 4 carbon atoms, an alkyloxycarbonyl group having 1 to 4 carbon atoms, a cyano group, etc. More specifically, examples of the optionally substituted cycloalkyl group include 1-methylcyclopropyl, 2,2-dimethylcyclopropyl, 2-chlorocyclopropyl, 2,2-dichlorocyclopropyl, 2-methoxycarbonylcyclopropyl, 2-cyanocyclopropyl, 2-methylcyclopentyl and 3-methylcyclopentyl groups, etc.

Examples of the aralkyl group having 7 to 11 carbon atoms, represented by $R^5$, include benzyl, 1-phenylethyl, 2-phenylethyl, 1-phenylpropyl, 1-naphthylmethyl and 2-naphthylmethyl groups, etc., and these aralkyl groups may be substituted on their aromatic rings with at least one substituent such as a halogen atom, an alkyl group having 1 to 12 carbon atoms, a haloalkyl group having 1 to 6 carbon atoms, an alkyloxy group having 1 to 6 carbon atoms, a haloalkyloxy group having 1 to 6 carbon atoms, an alkylthio group having 1 to 6 carbon atoms, an alkylsulfonyl group having 1 to 6 carbon atoms, an alkyloxycarbonyl group having 1 to 6 carbon atoms, a carboxy group, an optionally substituted carbamoyl group, a cyano group, a nitro group, etc. More specifically, examples of the optionally substituted aralkyl group include benzyl, 2-fluorobenzyl, 3-fluorobenzyl, 4-fluorobenzyl, 2-chlorobenzyl, 3-chlorobenzyl, 4-chlorobenzyl, 2-bromobenzyl, 3-bromobenzyl, 4-bromobenzyl, 3,5-difluorobenzyl, 3,5-dichlorobenzyl, 3,5-dibromobenzyl, 2-methylbenzyl, 3-methylbenzyl, 4-methylbenzyl, 2,4-dimethylbenzyl, 3,5-dimethylbenzyl, 2-trifluoromethylbenzyl, 3-trifluoromethylbenzyl, 4-trifluoromethylbenzyl, 3,5-bis(trifluoromethyl)benzyl, 2,4-bis(trifluoromethyl)benzyl, 2-methoxycarbonylbenzyl, 3-methoxycarbonylbenzyl, 4-methoxycarbonylbenzyl, 3-carboxybenzyl, 4-carboxybenzyl, 3-(N,N-dimethylcarbamoyl)benzyl, 4-(N,N-dimethylcarbamoyl)benzyl, 3-(N,N-diethylcarbamoyl)benzyl, 3-(N-ethyl-N-propylcarbamoyl)benzyl, 3-cyanobenzyl, 4-cyanobenzyl, 2-methoxybenzyl, 3-methoxybenzyl, 4-methoxybenzyl, 3,4-dimethoxybenzyl, 4-trifluoromethoxybenzyl, 4-phenoxybenzyl, 4-methylthiobenzyl, 4-methylsulfonylbenzyl, 2-nitrobenzyl, 3-nitrobenzyl, 4-nitrobenzyl, 1-(2-fluorophenyl)ethyl, 1-(2-chlorophenyl)ethyl, 1-(2-bromophenyl)ethyl, 1-(3-fluorophenyl)ethyl, 1-(3-chlorophenyl)ethyl, 1-(3-bromophenyl)ethyl, 1-(4-fluorophenyl)ethyl, 1-(4-chlorophenyl)ethyl, 1-(4-bromophenyl)ethyl, 1-(2-trifluoromethylphenyl)ethyl, 1-(3-trifluoromethylphenyl)ethyl, 1-(4-trifluoromethylphenyl)ethyl, 2-(3-bromophenyl)ethyl, 2-(3-trifluoromethylphenyl)ethyl, 3-phenylpropyl and 4-phenylbutyl groups, etc.

Examples of the alkenyl group having 3 to 6 carbon atoms, represented by $R^5$, include allyl, 2-methyl-2-propenyl, 2-butenyl, 3-butenyl, 2-pentenyl, 3-pentenyl, 2-hexenyl and 3-hexenyl groups, etc. Further, these alkenyl groups may be substituted with a halogen atom, etc., and examples of the optionally substituted alkenyl group include 2-chloro-2-propenyl, 3-chloropropenyl and 4-chloro-2-butenyl groups, etc.

The alkynyl group having 3 to 6 carbon atoms, represented by $R^5$, may be linear or branched, and examples thereof include propargyl, 1-butyn-3-yl, 3-methyl-1-butyn-3-yl, 2-buthynyl, 2-pentynyl and 3-pentynyl groups, etc. These alkynyl groups may be substituted with a halogen atom, etc., and examples of the optionally substituted alkynyl group include 3-fluoro-2-propynyl, 3-chloro-2-propynyl, 3-bromo-2-propynyl, 4-bromo-2-butynyl and 4-bromo-3-butynyl groups, etc.

Examples of the substituted phenyl group, represented by $R^5$, include phenyl groups which may have, as a substituent on the benzene ring, a halogen atom, an alkyl group having 1 to 12 carbon atoms, a haloalkyl group having 1 to 6 carbon atoms, an acyl group having 1 to 6 carbon atoms, an alkyl group having 1 to 12 carbon atoms and being substituted with an alkyloxyimino group having 1 to 4 carbon atoms, an alkyloxycarbonyl group having 1 to 6 carbon atoms, a carboxy group, a cyano group, an alkyloxy group having 1 to 6 carbon atoms, an aryloxy group, a haloalkyloxy group having 1 to 6 carbon atoms, an alkylthio group having 1 to 6 carbon atoms, an alkylsulfinyl group having 1 to 6 carbon atoms, an alkylsulfonyl group having 1 to 6 carbon atoms, a haloalkylthio group having 1 to 6 carbon atoms, a haloalkylsulfinyl group having 1 to 6 carbon atoms, a haloalkylsulfonyl group having 1 to 6 carbon atoms and a nitro group. More specifically, examples of the optionally substituted phenyl group include 2-fluorophenyl, 2-chlorophenyl, 2-bromophenyl, 3-fluorophenyl, 3-chlorophenyl, 4-fluorophenyl, 4-chlorophenyl, 4-bromophenyl, 2,4-difluorophenyl, 2,4-dichlorophenyl, 3,5-difluorophenyl, 3,5-dichlorophenyl, 3-chloro-2,4-difluorophenyl, 2,4,5-trchlorophenyl, 2,4-dichloro-3-methylphenyl, 2,4-dichloro-5-methoxyphenyl, 2,4-dichloro-5-isopropyloxyphenyl, 2-fluoro-4-chloro-5-methoxyphenyl, 2-fluoro-4-chloro-5-isopropyloxyphenyl, 2-fluoro-4-chloro-5-cyclopentyloxyphenyl, 2-fluoro-4-chloro-5-propargyloxyphenyl, 2-fluoro-4-chloro-5-(1-butyn-3-yloxy)phenyl, 2-fluoro-4-trifluoromethylphenyl, 2-chloro-4-trifluoromethylphenyl, 2-chloro-5-trifluoromethylphenyl, 4-fluoro-3-phenoxyphenyl, 2-fluoro-5-nitrophenyl, 2,4-difluoro-5-nitrophenyl, 2-methylphenyl, 3-methylphenyl, 4-methylphenyl, 2,4-dimethylphenyl, 4-ethylphenyl, 4-isopropylphenyl, 4-t-butylphenyl, 2-trifluoromethylphenyl, 3-trifluoromethylphenyl, 4-trifluoromethylphenyl, 2,4-bis(trifluoromethyl)phenyl, 3,5-bis(trifluoromethyl)phenyl, 2-acetylphenyl, 4-acetylphenyl, 4-isovalerylphenyl, 2-methoxycarbonylphenyl, 2-ethoxycarbonylphenyl, 3-methoxycarbonylphenyl, 4-methoxycarbonylphenyl, 2-carboxyphenyl, 4-carboxyphenyl, 2-cyanophenyl, 4-cyanophenyl, 2-methoxyphenyl, 3-methoxyphenyl, 4-methoxyphenyl, 3,4-dimethoxyphenyl, 4-isopropyloxyphenyl, 4-t-butyloxyphenyl, 3-trifluoromethyloxyphenyl, 4-trifluoromethyloxyphenyl, 3-phenoxyphenyl, 4-phenoxyphenyl, 2-methylthiophenyl, 4-methylthiophenyl, 2-methylsulfinylphenyl, 4-methylsulfinylphenyl, 2-methylsulfonylphenyl, 4-methylsulfonylphenyl, 4-trifluoromethylthiophenyl, 4-trifluoromethylsulfinylphenyl, 4-trifluoromethylsulfonylphenyl, 2-nitrophenyl and 4-nitrophenyl groups, etc.

Examples of the alkyloxy group having 1 to 6 carbon atoms, represented by $R^5$, include methoxy, ethoxy, propyloxy, isopropyloxy, butyloxy, isobutyloxy, s-butyloxy, t-butyloxy, pentyloxy and hexyloxy groups, etc., and these alkyloxy groups may be substituted with at least one substituent such as a halogen atom, a cycloalkyl group having 3 to 8 carbon atoms, an alkyloxy group having 1 to 6 carbon atoms, an alkylthio group having 1 to 6 carbon atoms, an alkyloxycarbonyl group having 1 to 6 carbon atoms, a carboxy group, a cyano group, a nitro group, an optionally substituted amino group, an optionally substituted phenyl group, etc.

Examples of the cycloalkyloxy group having 3 to 8 carbon atoms, represented by $R^5$, include cyclopropyloxy, cyclobutyloxy, cyclopentyloxy, cyclohexyloxy and cyclooctyloxy groups, etc., and these cycloalkyloxy groups may be substituted with a halogen atom, an alkyl group having 1 to 4 carbon atoms, an alkyloxycarbonyl group having 1 to 4 carbon atoms, a cyano group, etc. More specifically, examples of the optionally substituted cycloalkyloxy group include 1-methylcyclopropyloxy, 2,2-dimethylcyclopropyloxy, 2-chlorocyclopropyloxy, 2,2-dichlorocyclopropyloxy, 2-methoxycarbonylcyclopropyloxy, 2-cyanocyclopropyloxy, 2-methylcyclopentyloxy and 3-methylcyclopentyloxy groups, etc.

Examples of the aralkyloxy group having 7 to 11 carbon atoms, represented by $R^5$, include benzyloxy, 1-phenylethyloxy, 2-phenylethyloxy, 1-phenylpropyloxy, 1-naphthylmethyloxy and 2-naphthylmethyloxy groups, etc. These alkyloxy groups may have, on their aromatic rings, at least one substituent such as a halogen atom, an alkyl group having 1 to 12 carbon atoms, a haloalkyl group having 1 to 6 carbon atoms, an aralkyloxy group having 1 to 6 carbon atoms, a haloalkyloxy group having 1 to 6 carbon atoms, an alkylthio group having 1 to 6 carbon atoms, an alkylsulfonyl group having 1 to 6 carbon atoms, an alkyloxycarbonyl group having 1 to 6 carbon atoms, a carboxy group, an optionally substituted carbamoyl group, a cyano group, a nitro group, etc.

The alkenyloxy group having 3 to 6 carbon atoms, represented by $R^5$, may be linear, branched or cyclic, and examples thereof include 1-propenyloxy, allyloxy, 2-methyl-2-propenyloxy, 2-butenyloxy, 3-butenyloxy, 2-pentenyloxy, 3-pentenyloxy, 1-cyclopentenyloxy, 2-hexenyloxy, 3-hexenyloxy, 1-cyclohexenyloxy, etc. Further, these alkenyloxy groups may be substituted with a halogen atom, etc., and examples of the optionally substituted alkenyloxy group include 2-chloro-2-propenyloxy, 3-chloropropenyloxy and 4-chloro-2-butenyloxy groups, etc.

The alkynyloxy group having 3 to 6 carbon atoms, represented by $R^5$, may be linear or branched, and examples thereof include propargyloxy, 1-butyn-3-yloxy, 3-methyl-1-butyn-3-yloxy, 2-butynyloxy, 2-pentynyloxy and 3-pentynyloxy groups, etc. Further, these alkynyloxy groups may be substituted with a halogen atom, etc., and examples of the optionally substituted alkynyloxy group include 3-fluoro-2-propynyloxy, 3-chloro-2-propynyloxy, 3-bromo-2-propynyloxy, 4-bromo-2-butynyloxy and 4-bromo-3-butynyloxy groups, etc.

Examples of the optionally substituted phenyloxy group, represented by $R^5$, include phenyloxy groups which may have, on their benzene rings, at least one substituent such as a halogen atom, an alkyl group having 1 to 12 carbon atoms, a haloalkyl group having 1 to 6 carbon atoms, an alkyloxy group having 1 to 6 carbon atoms, a haloalkyloxy group having 1 to 6 carbon atoms, an alkylthio group having 1 to 6 carbon atoms, an alkylsulfinyl group having 1 to 6 carbon atoms, an alkylsulfonyl group having 1 to 6 carbon atoms, an alkyloxycarbonyl group having 1 to 6 carbon atoms, a carboxy group, an optionally substituted carbamoyl group, a cyano group, a nitro group, etc.

In the present invention, from the viewpoint of herbicidal activity of pyrazole derivatives of the general formula (8), preferably, $R^1$ is a methyl group, $R^2$ is a hydrogen atom and $R^5$ is an alkyl group having 1 to 12 carbon atoms, or preferably, $R^{4a}$ is 2-chloro-6-fluoro-4-trifluoromethylphenyl or 2,6-dichloro-4-trifluoromethylphenyl group. Further, preferably, Y is an oxygen atom.

A reaction scheme in the above production process 4 is shown below.

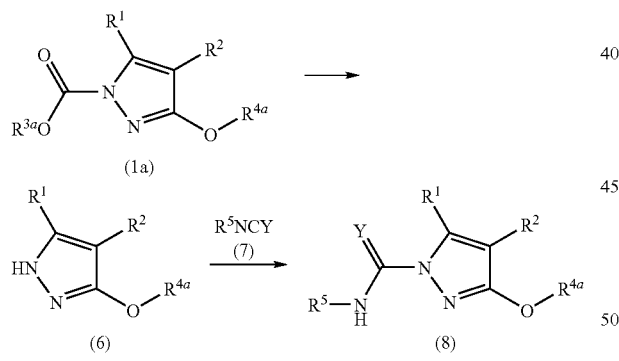

wherein $R^1$, $R^2$, $R^{3a}$, $R^{4a}$, $R^5$ and Y are as defined above.

In this reaction, the step of hydrolyzing 3-aryloxypyrazole-1-carboxylate derivatives of the general formula (1a) to generate 3-aryloxypyrazole derivatives of the general formula (6) is as explained with regard to the aforementioned production process 3.

The reaction between 3-aryloxypyrazole derivatives of the general formula (6) and isocyanates or isothiocyanates of the general formula (7) can be carried out in the presence of a base. The base can be selected from alkali metal bases such as sodium hydride, sodium amide, sodium carbonate, potassium carbonate, sodium methoxide, sodium ethoxide, potassium-t-butoxide, sodium hydroxide, potassium hydroxide, etc., and organic amines such as triethylamine, tributylamine, N-methylmorpholine, pyridine, dimethylaniline, etc. The amount of the base to be used is not specially limited.

The reaction can be carried out in a solvent, and any solvent can be used so long as it has no detrimental effect on the reaction. The solvent can be selected, for example, from ether solvents such as diethyl ether, THF, dioxane, DME, etc., nitrile solvents such as acetonitrile, propionitrile, etc., esters such as ethyl acetate, ethyl propionate, etc., aromatic hydrocarbon solvents such as benzene, toluene, xylene, chlorobenzene, etc., halogen-containing solvents such as dichloromethane, chloroform, carbon tetrachloride, etc., amides such as DMF, N-methylpyrrolidone, etc., DMSO or mixtures of these solvents. The reaction temperature is not specially limited, while the reaction is carried out at a temperature selected from the range of 0° C. to 150° C., whereby the desired product can be obtained in good yields. After completion of the reaction, the desired product can be obtained by general post-treatment procedures, while it can be also purified by column chromatography, recrystallization, or the like if necessary.

In addition, pyrazole derivatives of the general formula (8a) can be produced by the following reaction, from 3-aryloxypyrazole derivatives of the general formula (6) obtained from 3-aryloxypyrazole-1-carboxylate derivatives of the general formula (1a) according to the production process 3.

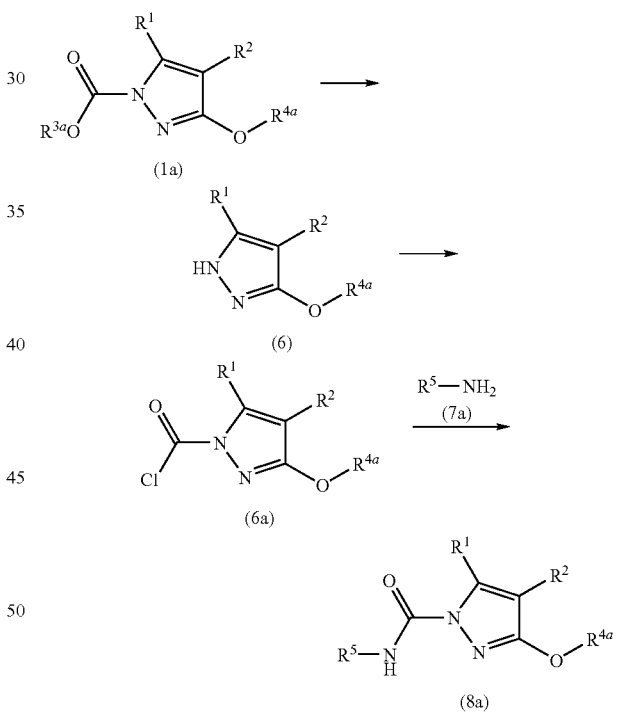

wherein $R^1$, $R^2$, $R^{4a}$, and $R^5$ are as defined above.

In this reaction, 3-aryloxypyrazole derivatives (6) and phosgene or phosgene equivalents are reacted in halogen-containing solvents such as dichloromethane, chloroform, carbon tetrachloride or the like, aromatic hydrocarbon solvents such as benzene, toluene, xylene, chlorobenzene or the like, or ester solvents such as ethyl acetate, propyl acetate or the like, to synthesize a compound (6a). The reaction temperature is not specially limited, while the reaction is carried out at a temperature selected from the range of –30° C. to 150° C., whereby the desired product can be obtained in good yields. After completion of the reaction, the desired product can be obtained by general post-treatment procedures, and the product obtained can be used in the subsequent reaction without isolating it.

Then, the compound (6a) is reacted with the amine compound (7a) to produce pyrazole derivatives (8a). Essentially, this reaction is carried out in the presence of a base. The base can be selected from alkali metal bases such as sodium hydride, sodium amide, sodium carbonate, potassium carbonate, potassium-t-butoxide, sodium hydroxide, potassium hydroxide, or the like, or organic amines such as triethylamine, tributylamine, N-methylmorpholine, pyridine, dimethylaniline, etc. The reaction is carried out using more than one equivalent of the base to the reaction substrate, whereby the desired product can be obtained in good yields.

The reaction is preferably carried out in an organic solvent, and the solvent can be selected from benzene, toluene, xylene, THF, diethyl ether, chloroform, dichloromethane, methanol, ethanol, propyl alcohol, isopropyl alcohol, t-butyl alcohol, ethyl acetate, DMF, DMSO, or the like. The reaction can be carried out at a temperature that is selected from the range of room temperature to a solvent reflux temperature as required. After completion of the reaction, the desired product can be obtained by general post-treatment procedures, while it can be purified by column chromatography, recrystallization, etc., if necessary.

Thus-obtained pyrazole derivatives of the general formula (8) exhibit excellent herbicidal activity without damaging crops. As pyrazole derivatives of the general formula (8), compounds of represented by

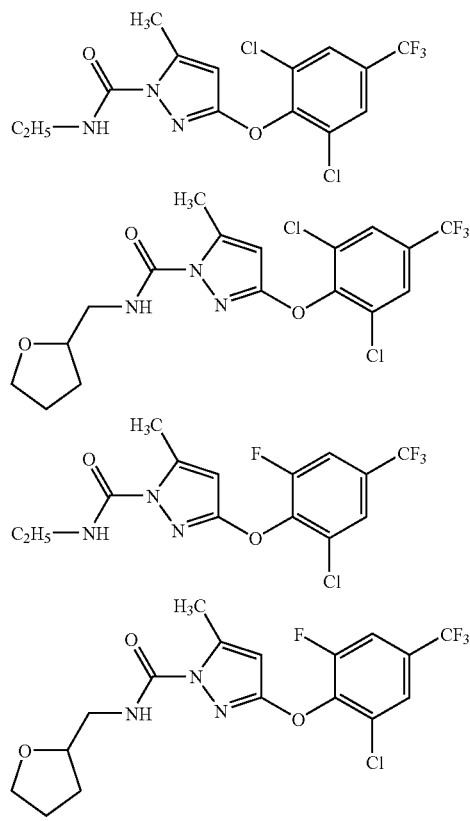

are particularly preferred in view of the above activity.

The present invention will be further explained in detail with reference to Examples hereinafter, while the present invention shall not be limited by these Examples.

Example 1

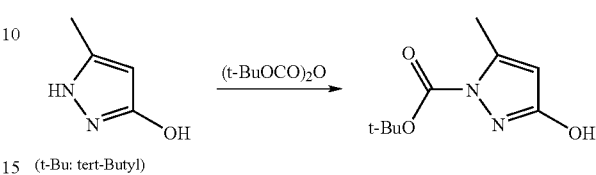

(t-Bu: tert-Butyl)

Triethylamine (320 mL, 2.3 mol) was added to a methanol (700 mL) solution of 3-hydroxy-5-methylpyrazole (225 g, 2.3 mol) and the mixture was stirred at 60° C. for 30 minutes. Then, a methanol (300 mL) solution of di-tert-butyl dicarbonate (500 g, 2.3 mol) was added dropwise, and the mixture was stirred under heating at 60° C. for 6 hours. After completion of the reaction, the reaction mixture was concentrated and precipitated crystals were washed with hexane and diethyl ether to give a white solid of tert-butyl 3-hydroxy-5-methylpyrazole-1-carboxylate (441.0 g, yield: 97.1%). Melting point: 169~171° C. (decomposed), $^1$H-NMR (DMSO, DMSO-$d_6$, ppm): δ1.53 (s, 9H), 2.37 (s, 3H), 5.70 (s, 1H). The hydroxy proton could not be assigned.

Example 2

3-Hydroxy-4,5-dimethylpyrazole and di-tert-butyl dicarbonate were reacted in the same manner as in Example 1 to give a white solid of tert-butyl 3-hydroxy-4,5-dimethylpyrazole-1-carboxylate. Melting point: 262~264° C. (decomposed), $^1$H-NMR (CDCl$_3$, TMS, ppm): δ1.63 (s, 9H), 1.87 (s, 3H), 2.40 (s, 3H), 12.50 (brs, 1H).

Example 3

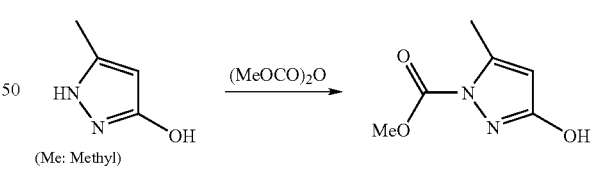

(Me: Methyl)

Triethylamine (13.0 mL, 93.2 mmol) was added to a methanol (90 mL) solution of 3-hydroxypyrazole (9.14 g, 93.0 mmol) and the mixture was stirred at room temperature for 10 minutes. Then, a methanol (10 mL) solution of dimethyl dicarbonate (12.0 mL, 112 mmol) was dropwise added with cooling in an ice-water bath, and the mixture was stirred at room temperature for 4 hours. After completion of the reaction, the reaction mixture was concentrated and precipitated crystals were washed with hexane and diethyl ether to give a white solid of methyl 3-hydroxy-5-methylpyrazole-1-carboxylate (11.7 g, yield: 80.5%). Melting point: 181~183°

C. (decomposed), $^1$H-NMR (DMSO, DMSO-d$_6$, ppm): δ2.40 (d, J=0.9 Hz, 3H), 3.85 (s, 3H), 5.76 (d, J=0.9 Hz, 1H), 10.71 (s, 1H).

Example 4

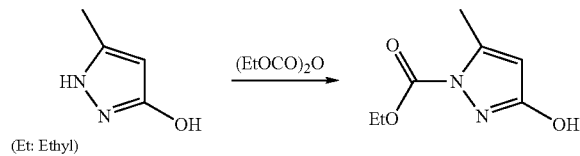

(Et: Ethyl)

Triethylamine (3.5 mL, 25.0 mmol) was added to an ethanol (25 mL) solution of 3-hydroxypyrazole (2.45 g, 25.0 mmol), and the mixture was stirred at room temperature for 10 minutes. Then, an ethanol (5 mL) solution of diethyl dicarbonate (3.8 mL, 25.7 mmol) was dropwise added with cooling in an ice-water bath, and the mixture was stirred at room temperature for 3 hours. After completion of the reaction, the reaction mixture was concentrated and precipitated crystals were washed with hexane and diethyl ether to give a white solid of ethyl 3-hydroxy-5-methylpyrazole-1-carboxylate (3.1 g, yield: 71.7%). Melting point: 198~200° C. (decomposed), $^1$H-NMR (DMSO, DMSO-d$_6$, ppm): δ1.31 (t, J=7.1 Hz, 3H), 2.41 (m, 3H), 4.31 (q, J=7.1 Hz, 2H), 5.76 (d, J=0.8 Hz, 1H), 10.77 (brs, 1H).

Example 5

A DMSO (50 mL) solution of 3-chloro-4,5-difluorobenzotrifluoride (40.0 g, g, 185 mmol) was added to a DMSO (250 mL) solution of tert-butyl 3-hydroxy-5-methylpyrazole-1-carboxylate (33.0 g, 166 mmol) and potassium carbonate (28.1 g, 203 mmol), and the mixture was stirred under heating at 80° C. for 2 hours. After completion of the reaction, the reaction mixture was poured into a 2 mol/L hydrochloric acid (1 L), and precipitated crystals were consecutively washed with water, a 0.1 mol/L sodium hydroxide aqueous solution and hexane to give a white solid of tert-butyl 3-(2-chloro-6-fluoro-4-trifluoromethylphenyloxy)-5-methylpyrazole-1-carboxylate (59.5 g, yield: 90.7%). Melting point: 142~144° C., $^1$H-NMR (CDCl$_3$, TMS, ppm): δ1.59 (s, 9H), 2.49 (d, J=0.7 Hz, 3H), 5.78 (d, J=0.7 Hz, 1H), 7.37 (dd, J=2.1 Hz, J$_{HF}$=9.4 Hz, 1H), 7.54 (m, 1H).

Examples 6-10

A tert-butyl 3-hydroxypyrazole-1-carboxylate derivative and halo-substituted benzene or halo-substituted pyridine were reacted in the same manner as in Example 5 to give a corresponding tert-butyl 3-(substituted phenyloxy)pyrazole-1-carboxylate derivative or tert-butyl 3-(substituted pyridyloxy)pyrazole-1-carboxylate. Products/forms/yields/melting points/NMR spectrum data are described below.

Example 6 tert-Butyl 3-(2-nitro-4-trifluoromethylphenyloxy)-5-methylpyrazole-1-carboxylate/yellowish solid/yield: 62.2%/melting point: 68~70° C./$^1$H-NMR (CDCl$_3$, TMS, ppm): δ1.61 (s, 9H), 2.53 (d, J=0.6 Hz, 3H), 5.92 (d, J=0.6 Hz, 1H), 7.64 (d, J=8.7 Hz, 1H), 7.82 (dd, J=1.9 Hz and 8.7 Hz, 1H), 8.23 (d, J=1.9 Hz, 1H).

Example 7 tert-Butyl 3-(2,6-dichloro-4-trifluoromethylphenyloxy)-5-methylpyrazole-1-carboxylate/white solid/yield: 95.8%/melting point: 159~161° C./$^1$H-NMR (CDCl$_3$, TMS, ppm): δ1.60 (s, 9H), 2.48 (d, J=0.8 Hz, 3H), 5.70 (d, J=0.8 Hz, 1H), 7.63 (s, 2H).

Example 8 tert-Butyl 3-(2-chloro-6-nitro-4-trifluoromethylphenyloxy)-5-methylpyrazole-1-carboxylate/white solid/yield: 41.0%/melting point: 119~121° C./$^1$H-NMR (CDCl$_3$, TMS, ppm): δ1.57 (s, 9H), 2.49 (d, J=0.8 Hz, 3H), 5.92 (d, J=0.8 Hz, 1H), 7.98 (d, J=2.1 Hz, 1H), 8.19 (d, J=2.1 Hz, 1H).

Example 9 tert-Butyl 3-(3-chloro-5-trifluoromethylpyridin-2-yloxy)-5-methylpyrazole-1-carboxylate/white solid/yield: 90.5%/melting point: 90~92° C./$^1$H-NMR (CDCl$_3$, TMS, ppm): δ1.64 (s, 9H), 2.58 (d, J=0.7 Hz, 3H), 6.08 (d, J=0.7 Hz, 1H), 7.99 (d, J=2.1 Hz, 1H), 8.25~8.40 (m, 1H).

Example 10 tert-Butyl 3-(2-chloro-6-fluoro-4-trifluoromethylphenyloxy)-4,5-dimethylpyrazole-1-carboxylate/white solid/yield: 54.6%/melting point: 138~139° C./$^1$H-NMR (CDCl$_3$, TMS, ppm): δ1.56 (s, 9H), 2.02 (d, J=0.4 Hz, 3H), 2.40 (d, J=0.4 Hz, 3H), 7.36 (dd, J=2.1 Hz, J$_{HF}$=9.4 Hz, 1H), 7.45~7.55 (m, 1H).

Example 11

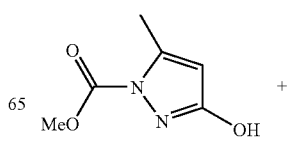

-continued

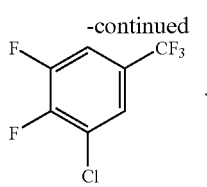

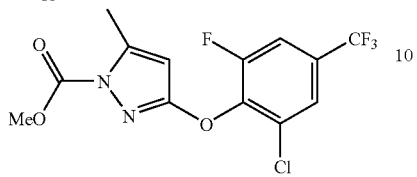

To a DMSO (15 mL) solution of methyl 3-hydroxy-5-methylpyrazole-1-carboxylate (1.56 g, 10.0 mmol) and potassium carbonate (1.38 g, 10.0 mmol) was added 3-chloro-4,5-difluorobenzotrifluoride (2.21 g, 10.0 mmol), and the mixture was stirred under heating at 40° C. for 8 hours. After completion of the reaction, the reaction mixture was poured into 2 mol/L hydrochloric acid (30 mL) and extracted with ethyl acetate. The organic layers combined were washed with water, and dried over anhydrous magnesium sulfate, and the solvent was distilled off. The thus-obtained residue was purified by silica gel column chromatography (ethyl acetate:hexane=1:5) to give a white solid of methyl 3-(2-chloro-6-fluoro-4-trifluoromethylphenyloxy)-5-methylpyrazole-1-carboxylate (1.60 g, yield: 45.4%). Melting point: 123~125° C., $^1$H-NMR (CDCl$_3$, TMS, ppm): δ2.55 (d, J=0.8 Hz, 3H), 3.94 (s, 3H), 5.87 (d, J=0.8 Hz, 1H), 7.38 (dd, J=2.0 Hz, J$_{HF}$=9.4 Hz, 1H), 7.50~7.60 (m, 1H).

Example 12

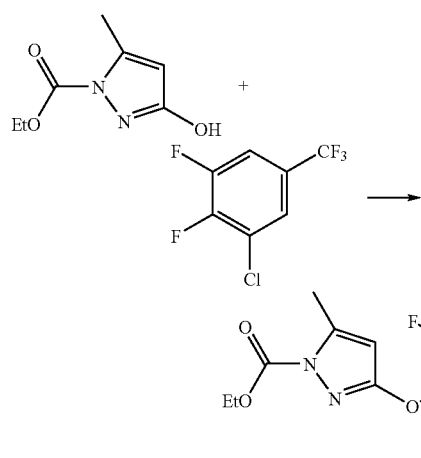

To a DMSO (15 mL) solution of ethyl 3-hydroxy-5-methylpyrazole-1-carboxylate (1.36 g, 8.0 mmol) and potassium carbonate (1.1 g, 8.0 mmol) was added 3-chloro-4,5-difluorobenzotrifluoride (1.77 g, 8.0 mmol) and the mixture was stirred under heating at 40° C. for 8 hours. After completion of the reaction, the reaction mixture was poured into 2 mol/L hydrochloric acid (30 mL) and extracted with ethyl acetate. The organic layers combined were washed with water, and dried over anhydrous magnesium sulfate, and the solvent was distilled off. The thus-obtained residue was purified by silica gel column chromatography (ethyl acetate:hexane=1:7~1:5) to give a white solid of ethyl 3-(2-chloro-6-fluoro-4-trifluoromethylphenyloxy)-5-methylpyrazole-1-carboxylate (2.14 g, yield: 72.9%). Melting point: 127~129° C., $^1$H-NMR (CDCl$_3$, TMS, ppm): δ1.40 (t, J=7.1 Hz, 3H), 2.53 (d, J=0.8 Hz, 3H), 4.41 (q, J=7.1 Hz, 2H), 5.81 (d, J=0.8 Hz, 1H), 7.38 (dd, J=2.1 Hz, J$_{HF}$=9.5 Hz, 1H), 7.50~7.60 (m, 1H).

Example 13

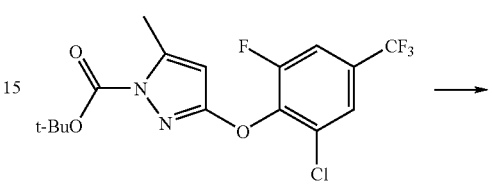

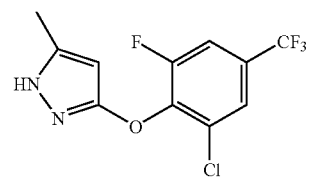

To an ethyl acetate (100 mL) solution of tert-butyl 3-(2-chloro-6-fluoro-4-trifluoromethylphenyloxy)-5-methylpyrazole-1-carboxylate (49.7 g, 126 mmol) was added 3 mol/L of HCL (40 mL), and the mixture was refluxed under heating for 2 hours. After completion of the reaction, the reaction mixture was consecutively washed with water and a 1 mol/L sodium hydroxide aqueous solution and dried over anhydrous magnesium sulfate, and the solvent was distilled off to give a white solid of 3-(2-chloro-6-fluoro-4-trifluoromethylphenyloxy)-5-methylpyrazole (33.0 g, yield: 89.0%). Melting point: 116~117° C., $^1$H-NMR (CDCl$_3$, TMS, ppm): δ2.24 (s, 3H), 5.69 (s, 1H), 7.36 (dd, J=1.8 Hz, J$_{HF}$=9.4 Hz, 1H), 7.50-7.60 (m, 1H), 9.00-9.30 (brs, 1H).

Examples 14 and 15 tert-Butyl 3-(substituted phenyloxy)pyrazole-1-carboxylate or tert-butyl 3-(substituted pyridyloxy)pyrazole-1-carboxylate was hydrolyzed in the presence of 3 mol/L HCL in the same manner as in Example 13, to give a corresponding 3-(substituted phenyloxy)pyrazole or 3-(substituted pyridyloxy)pyrazole derivative. Products/forms/yields/melting points/NMR spectrum data are described below.

Example 14

3-(2,6-dichloro-4-trifluoromethylphenyloxy)-5-methylpyrazole/white solid/yield: 91.4%/Melting point: 153~155° C./$^1$H-NMR (CDCl$_3$, TMS, ppm): δ2.27 (s, 3H), 5.68 (s, 1H), 7.64 (s, 2H), 8.75~9.70 (brs, 1H).

Example 15

3-(3-chloro-5-trifluoromethylpyridin-2-yloxy)-5-methylpyrazole/white solid/yield: 86.4%/Melting point: 109~111° C./¹H-NMR (CDCl₃, TMS, ppm): δ2.32 (s, 3H), 5.86 (s, 1H), 7.77 (d, J=2.3 Hz, 1H), 8.03 (d, J=2.3 Hz, 1H), 9.40~11.50 (brs, 1H).

Example 16

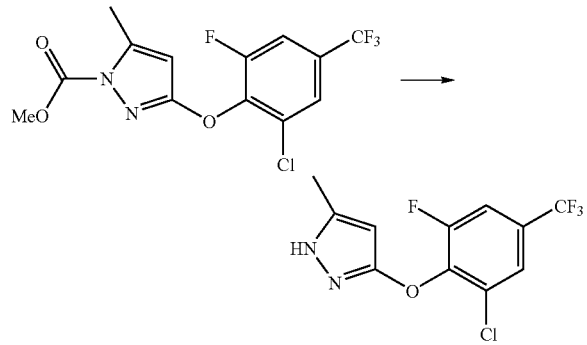

To an ethanol (10 mL) solution of methyl 3-(2-chloro-6-fluoro-4-trifluoromethylphenyloxy)-5-methylpyrazole-1-carboxylate (0.53 g, 1.5 mmol) was added 5% sodium hydroxide (8 mL), and the mixture was refluxed under heating for 2 hours. After completion of the reaction, the solvent was distilled off the reaction mixture, and then water was added, followed by extraction with ethyl acetate. The organic layers combined were washed with water, and dried over anhydrous magnesium sulfate and the solvent was distilled off. The resultant residue was purified by silica gel column chromatography (ethyl acetate:hexane=1:5) to give a white solid of 3-(2-chloro-6-fluoro-4-trifluoromethylphenyloxy)-5-methylpyrazole (0.39 g, yield: 88.2%).

Example 17

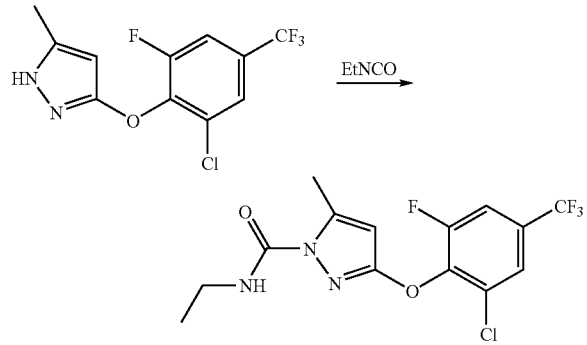

Triethylamine (2.02 g, 20.0 mmol) and ethyl isocyanate (1.42 g, 20.0 mmol) were added to an ethyl acetate (50 mL) solution of 3-(2-chloro-6-fluoro-4-trifluoromethylphenyloxy)-5-methylpyrazole (5.33 g, 18.0 mmol), and the mixture was stirred at room temperature for 4 hours. After completion of the reaction, the reaction mixture was poured into 2 mol/L hydrochloric acid, followed by extraction with ethyl acetate (50 mL×3 times). The organic layer was washed with water and dried over anhydrous magnesium sulfate. Then, the desiccant was removed by filtering and the solvent was distilled off the filtrate under reduced pressure. The resultant crude product was purified with a silica gel column (ethyl acetate/hexane=1/10) to give a white solid of N-ethyl-3-(2-chloro-6-fluoro-4-trifluoromethylphenyloxy)-5-methylpyrazole-1-carboxamide (5.37 g, yield: 81.6%). Melting point: 84~86° C., ¹H-NMR (Acetone-d₆, Acetone, ppm): δ1.10 (t, J=7.2 Hz, 3H), 2.55 (d, J=0.9 Hz, 3H), 3.26 (dq, J=6.1 and 7.2 Hz, 2H), 5.98 (q, J=0.9 Hz, 1H), 7.39~7.48 (brt, J=6.1 Hz, 1H), 7.75 (ddq, J=2.1 and $J_{HF}$=0.7 and 9.7 Hz, 1H), 7.82 (dq, 1H, J=2.1 and $J_{HF}$=0.7 Hz).

Example 18

3-(2,6-Dichloro-4-trifluoromethylphenyloxy)-5-methylpyrazole was reacted with ethyl isocyanate in the same manner as in Example 17 to give a white solid of N-ethyl-3-(2,6-dichloro-4-trifluoromethylphenyloxy)-5-methylpyrazole-1-carboxamide (5.37 g, yield: 62.8%). Melting point: 80~82° C., ¹H-NMR (Acetone-d₆, Acetone, ppm): δ1.10 (t, J=7.2 Hz, 3H), 2.55 (d, J=0.8 Hz, 3H), 3.25 (dq, J=6.1 and 7.2 Hz, 2H), 5.71 (q, J=0.8 Hz, 1H), 7.37~7.48 (brt, 1H, J=6.1 Hz), 7.67 (q, 2H, $J_{HF}$=0.7 Hz).

Referential Example 1

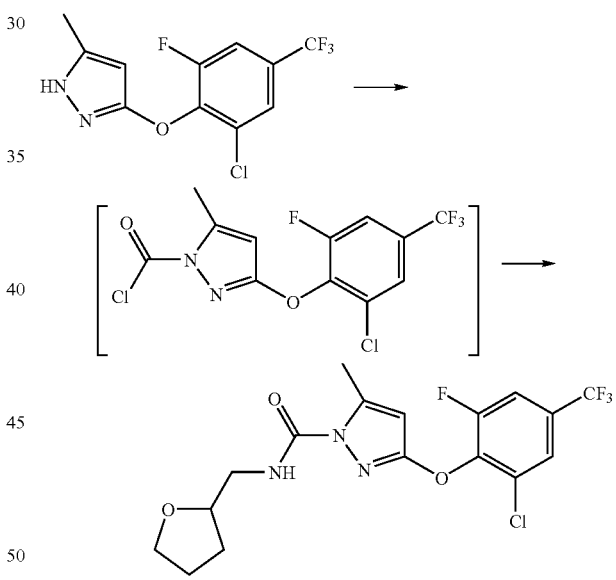

Trichloromethyl chloroformate (0.39 g, 2.0 mmol) was added to a chloroform (10 mL) solution of 3-(2-chloro-6-fluoro-4-trifluoromethylphenyloxy)-5-methylpyrazole (0.59 g, 2.0 mmol) at 0° C., and while the mixture was allowed to gradually warm up to a room temperature, it was further stirred at room temperature for 3 hours. Tetrahydrofurfurylamine (0.61 g, 6.0 mmol) and triethylamine (0.4 g, 4.0 mmol) were added to the reaction mixture, and the mixture was refluxed under heating for 5 hours. After completion of the reaction, the reaction mixture was poured into ice and extracted with chloroform (20 mL×3 times). The organic layer was washed with water and dried over anhydrous magnesium sulfate, the desiccant was removed by filtering, and the solvent was distilled off the filtrate under reduced pressure. The resultant crude product was purified with a silica gel column (ethyl acetate/hexane=1/10~1/5) to give a colorless viscous substance of N-tetrahydrofurfuryl-3-(2-chloro-6-fluoro-4-trifluoromethylphenyloxy)-5-methylpyrazole-1-carboxamide (0.25 g, yield: 29.6%). $^1$H-NMR (CDCl$_3$, TMS, ppm): δ1.50-1.65 (m, 1H), 1.75~2.05 (m, 3H), 2.58 (s, 3H), 3.32 (dt, J=6.3 and 13.9 Hz, 1H), 3.48 (ddd, J=3.7, 5.7 and 13.9 Hz, 1H), 3.74 (dq, J=7.0 and 8.6 Hz, 2H), 4.03 (dq, J=3.7 and 7.0 Hz, 1H), 5.79 (s, 1H), 6.85~7.10 (m, 1H), 7.39 (dd, J=1.9 and J$_{HF}$=9.3 Hz, 1H), 7.56 (s, 1H).

Referential Example 2

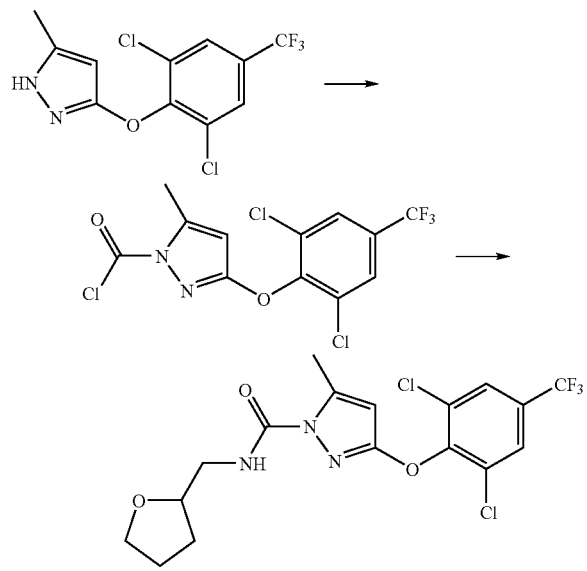

Trichloromethyl chloroformate (0.49 g, 2.5 mmol) was added to a chloroform (10 mL) solution of 3-(2,6-dichloro-4-trifluoromethylphenyloxy)-5-methylpyrazole (0.78 g, 2.5 mmol) at 0° C., and while the mixture was allowed to gradually warm up to a room temperature, it was further stirred at room temperature for 3 hours. Tetrahydrofurfurylamine (0.51 g, 5.0 mmol) and triethylamine (1.01 g, 10 mmol) were added to the reaction mixture, and the mixture was refluxed under heating for 4 hours. After completion of the reaction, the reaction mixture was poured into ice and extracted with chloroform (20 mL×3 times). The organic layer was washed with water and dried over anhydrous magnesium sulfate, the desiccant was removed by filtering, and the solvent was distilled off the filtrate under reduced pressure. The resultant crude product was purified with a silica gel column (ethyl acetate: hexane=1:7) to give a white solid of N-tetrahydrofurfuryl-3-(2,6-dichloro-4-trifluoromethylphenyloxy)-5-methylpyrazole-1-carboxamide (0.31 g, yield: 28.3%). Melting point: 74~76° C., $^1$H-NMR (CDCl$_3$, TMS, ppm): δ1.45~1.65 (m, 1H), 1.75-2.05 (m, 3H), 2.58 (d, J=0.8 Hz, 3H), 3.32 (dt, J=6.2 and 13.9 Hz, 1H), 3.47 (ddd, J=3.7, 5.6 and 13.9 Hz, 1H), 3.60~3.85 (m, 2H), 3.95~4.15 (m, 1H), 5.75 (q, J=0.8 Hz, 1H), 6.85~7.15 (m, 1H), 7.66 (s, 2H).

INDUSTRIAL UTILITY

The pyrazole-1-carboxylate derivative of the present invention is useful as an intermediate for the production of 3-aryloxypyrazole-1-carboxamide derivative having herbicidal activities. According to the present invention, further, the above pyrazole-1-carboxylate derivative can be industrially advantageously produced, and when this compound is used, the pyrazole derivative having herbicidal activities can be efficiently produced.

The invention claimed is:

1. A pyrazole-1-carboxylate derivative of a general formula (I),

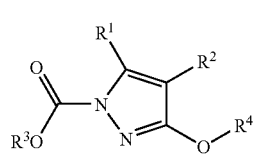

(1)

wherein R$^1$ is a hydrogen atom or an optionally substituted alkyl group having 1 to 6 carbon atoms, R$^2$ is a hydrogen atom, R$^3$ is an optionally substituted alkyl group having 1 to 6 carbon atoms and R$^4$ is a hydrogen atom, an optionally substituted phenyl group or an optionally substituted pyridyl group, provided that the case of R$^3$ being an ethyl group is excluded when R$^2$ and R$^4$ are hydrogen atoms and R$^1$ is a methyl group, when R$^2$ and R$^4$ are hydrogen atoms and R$^1$ is a propyl group or when R$^2$ is an ethyl group, R$^4$ is a hydrogen atom and R$^1$ is a methyl group.

2. A pyrazole-1-carboxylate derivative of claim 1, which has a general formula (1) in which R$^1$ is a methyl group, R$^2$ is a hydrogen atom and R$^3$ is an alkyl group having 1 to 4 carbon atoms.

3. A pyrazole-1-carboxylate derivative of claim 1 or 2, wherein R$^4$ is a hydrogen atom, 2-chloro-6-fluoro-4-trifluoromethylphenyl group or 2,6-dichloro-4-trifluoromethylphenyl group.

4. A process for production of 3-hydroxypyrazole-1-carboxylate derivatives of a general formula (4),

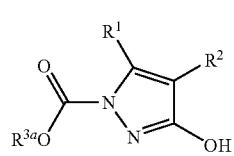

(4)

wherein R$^1$ is a hydrogen atom or an optionally substituted alkyl group having 1 to 6 carbon atoms, R$^2$ is a hydrogen atom and R$^{3a}$ is an optionally substituted alkyl group having 1 to 6 carbon atoms, which comprises reacting 3-hydroxypyrazole derivatives of a general formula (2),

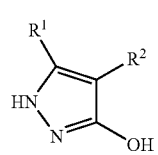

(2)

wherein $R^1$ and $R^2$ are as defined above, with dialkyl dicarbonates of a general formula (3),

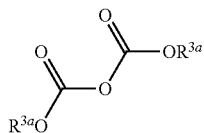

(3)

wherein $R^{3a}$ is as defined above.

5. A process for production of 3-aryloxypyrazole-1-carboxylate derivatives of a general formula (1a),

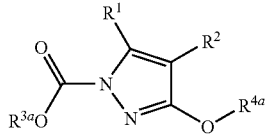

(1a)

wherein $R^1$ is a hydrogen atom or an optionally substituted alkyl group having 1 to 6 carbon atoms, $R^2$ is a hydrogen atom and $R^{3a}$ is an optionally substituted alkyl group having 1 to 6 carbon atoms, and $R^{4a}$ is an optionally substituted phenyl group or an optionally substituted pyridyl group, which comprises reacting 3-hydroxypyrazole-1-carboxylate derivatives of a general formula (4),

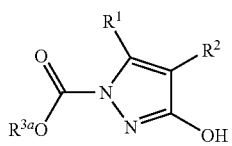

(4)

wherein $R^1$, $R^2$ and $R^{3a}$ are as defined above, with aryl halides of a general formula (5), $$R^{4a}\text{-}Z \quad (5)$$

wherein $R^{4a}$ is as defined above and Z is a halogen atom, in the presence of a base.

6. A process for production of 3-aryloxypyrazole derivatives of a general formula (6), (6)

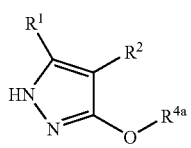

wherein $R^1$ is a hydrogen atom or an optionally substituted alkyl group having 1 to 6 carbon atoms, $R^2$ is a hydrogen atom and $R^{4a}$ is an optionally substituted phenyl group or an optionally substituted pyridyl group, which comprises hydrolyzing 3-aryloxypyrazole-1-carboxylate derivatives of a general formula (1a),

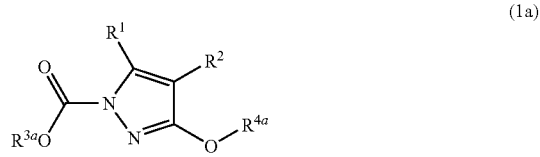

(1a)

wherein $R^1$, $R^2$, $R^{3a}$ and $R^{4a}$ are as defined above.

7. A process for production of pyrazole derivatives of a general formula (8),

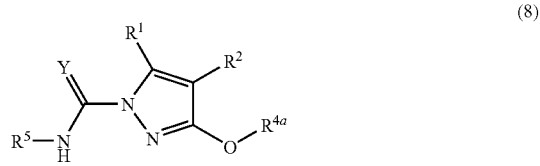

(8)

wherein $R^1$ is a hydrogen atom or an optionally substituted alkyl group having 1 to 6 carbon atoms, $R^2$ is a hydrogen atom and $R^{4a}$ is an optionally substituted phenyl group or an optionally substituted pyridyl group, $R^5$ is an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms, an optionally substituted phenyl group, an optionally substituted alkyloxy group having 1 to 6 carbon atoms, an optionally substituted cycloalkyloxy group having 3 to 8 carbon atoms, an optionally substituted aralkyloxy group having 7 to 11 carbon atoms, an optionally substituted alkenyloxy group having 3 to 6 carbon atoms, an optionally substituted alkynyloxy group having 3 to 6 carbon atoms or an optionally substituted phenyloxy group and Y is an oxygen atom or a sulfur atom, which comprises hydrolyzing 3-aryloxypyrazole-1-carboxylate derivatives of a general formula (1a),

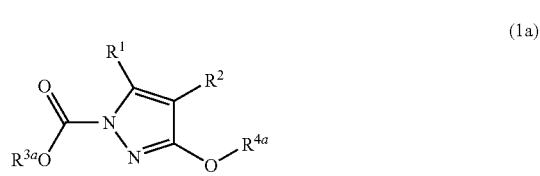

(1a)

wherein $R^1$, $R^2$, $R^{1a}$ and $R^{4a}$ are as defined above, to obtain 3-aryloxypyrazole derivatives of a general formula (6), (6)

wherein $R^1$, $R^2$ and $R^{4a}$ are as defined above, and then reacting this product with isocyanates or isothiocyanates of a general formula (7), $$R^5\text{—NCY} \quad (7)$$

wherein $R^5$ is an optionally substituted alkyl group having 1 to 12 carbon atoms, an optionally substituted cycloalkyl group having 3 to 8 carbon atoms, an optionally substituted aralkyl group having 7 to 11 carbon atoms, an optionally substituted alkenyl group having 3 to 6 carbon atoms, an optionally substituted alkynyl group having 3 to 6 carbon atoms, an optionally substituted phenyl group, an optionally substituted alkyloxy group having 1 to 6 carbon atoms, an optionally substituted cycloalkyloxy group having 3 to 8 carbon atoms, an optionally substituted aralkyloxy group having 7 to 11 carbon atoms, an optionally substituted alkenyloxy group having 3 to 6 carbon atoms, an optionally substituted alkynyloxy group having 3 to 6 carbon atoms or an optionally substituted phenyloxy group and Y is an oxygen atom or a sulfur atom.

\* \* \* \* \*